United States Patent
Lin et al.

(10) Patent No.: US 7,838,038 B2
(45) Date of Patent: Nov. 23, 2010

(54) BIOMATERIAL AND PREPARATION METHOD THEREOF

(76) Inventors: Chien-Cheng Lin, No. 2, Furong St., Shilin District, Taipei City (TW) 111; Horng-Ji Lai, 6F., No. 11, Alley 78, Lane 208, Rui An St., Taipei (TW) 106; Shang-Ming Lin, 2F., No. 16, Lane 103, Huihu St., Fongyuan City, Taichung County (TW) 420

( * ) Notice: Subject to any disclaimer, the term of this patent is extended or adjusted under 35 U.S.C. 154(b) by 199 days.

(21) Appl. No.: 11/882,328

(22) Filed: Jul. 31, 2007

(65) Prior Publication Data

US 2008/0128536 A1     Jun. 5, 2008

Related U.S. Application Data

(60) Provisional application No. 60/868,409, filed on Dec. 4, 2006.

(51) Int. Cl.
*A61K 35/60* (2006.01)
(52) U.S. Cl. .................. 424/522; 424/520; 424/572

(58) Field of Classification Search ............... 424/520, 424/522, 572
See application file for complete search history.

(56) References Cited

U.S. PATENT DOCUMENTS

| | | | |
|---|---|---|---|
| 2002/0006422 A1* | 1/2002 | Koda et al. | 424/401 |
| 2003/0118715 A1* | 6/2003 | Helgason | 426/624 |

* cited by examiner

*Primary Examiner*—Ruth A Davis
(74) *Attorney, Agent, or Firm*—Bacon & Thomas, PLLC

(57) ABSTRACT

A biomaterial prepared from a process comprising dehydrating the fish scales until the fish scales containing less than about 50% of water, and grinding the dehydrated fish scales into ground particles each having an average size of less than about 10,000 μm in diameter, wherein the ground particles contain a mixture of sponge like matrix and powder is provided. The invention also provides a biomaterial prepared from fish scales by a process comprising subjecting the fish scales to a heat treatment at a temperature of less than about 200° C.

4 Claims, 6 Drawing Sheets
(2 of 6 Drawing Sheet(s) Filed in Color)

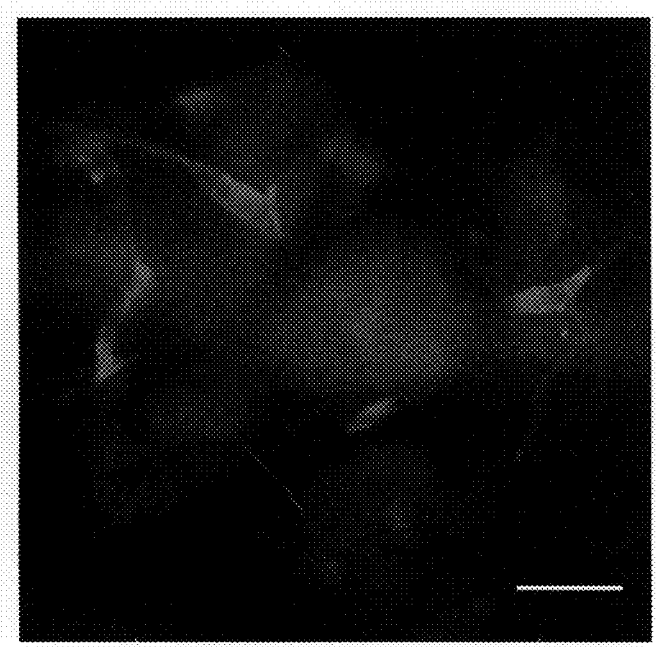
F I G. 3A
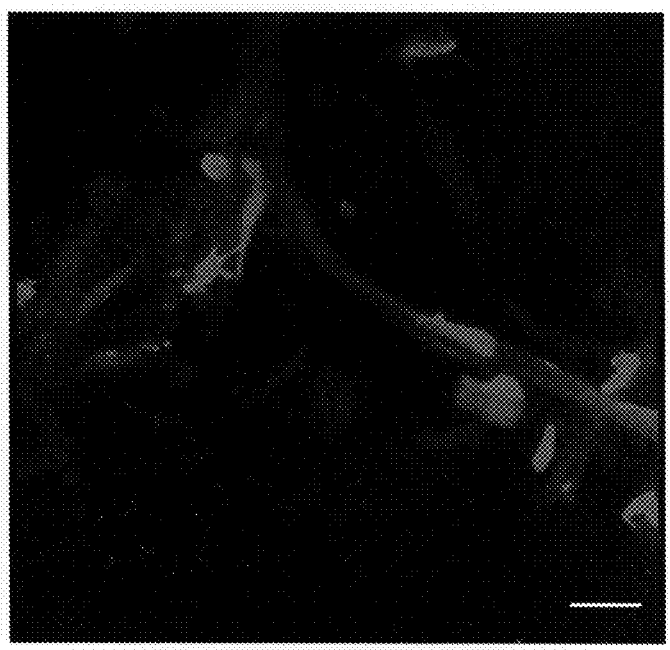
F I G. 3 B

US 7,838,038 B2

BIOMATERIAL AND PREPARATION METHOD THEREOF

BACKGROUND OF THE INVENTION

The present invention relates to a biomaterial and preparation method thereof, and particularly to a biomaterial prepared from fish scales for use in tissue repair and implantation.

Tissue engineering that involves the incorporation of a biomaterial with biologics and/or pharmaceutics and upon implantation in a patient will stimulate angiogenesis, tissue integration, and/or tissue remodeling. The biomaterial is a synthetic and biocompatible material that is used to construct artificial organs, rehabilitation devices, or prostheses and replace natural body tissues.

For over decades, collagen fiber, hydroxyapatite (HAP) and tri-calcium phosphate (TCP) are some biomaterials with great biocompatibility and safety to be used in human tissue implant. However, these biomaterials have disadvantages such as low mechanical strength, risk of chemical residue in cross linking, terrestrial animal transmitted disease.

Therefore, it is desirable to develop a biomaterial having a high mechanical strength, low possibility of contracting with the terrestrial contagious disease and is applicable to tissue repairs or implants.

BRIEF SUMMARY OF THE INVENTION

It is an aspect of the invention to provide a biomaterial prepared from fish scales by a process which includes dehydrating the fish scales until the fish scales containing less than about 50% of water, and grinding the dehydrated fish scales into ground particles having an average size of less than about 10,000 µm in diameter, wherein each of the ground particles contain a mixture of sponge like matrix and powder. In an embodiment of the invention, the fish scales contain less than about 25% of water, and the ground particles have an average size of less than about 5,000 µm in diameter.

It is another aspect of the invention to provide a biomaterial prepared from fish scales by a process, which comprises subjecting the fish scales to a heat treatment at a temperature of less than about 200° C.

It is a further aspect of the invention to provide a method for preparing a biomaterial. The method comprises dehydrating the fish scales until the fish scales containing less than about 50% of water, and grinding the dehydrated fish scales into ground particle each having an average size of less than about 10,000 µm in diameter, wherein the ground particles contain a mixture of sponge like matrix and powder. In an embodiment of the invention, the fish scales contain less than about 25% of water, and the ground particles have an average size of less than about 5,000 µm in diameter.

It is one other aspect of the invention to provide a method for preparing a biomaterial comprising subjecting the fish scales to a heat treatment at a temperature of less than about 200° C.

It is yet another aspect of the invention to provide a use of the biomaterial prepared by the process described above for repairing tissues.

It is yet a further aspect of the invention to provide a use of the biomaterial prepared by the process described above for tissue implantation.

BRIEF DESCRIPTION OF THE SEVERAL VIEWS OF THE DRAWINGS

The patent or application file contains at least one drawing executed in color. Copies of this patent or patent application publication with color drawing(s) will be provided by the office upon request and payment of the necessary fee.

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 1A is a flow chart illustrating a process for preparing a biomaterial in accordance with the invention.

FIG. 1B is a flow chart illustrating a process for preparing a biomaterial in accordance with examples 1 and 2 of the invention.

FIG. 1C is a flow chart illustrating a process for preparing a biomaterial in accordance with example 3 of the invention.

FIG. 2A is an SEM picture of 3T3 (fibroblast cell) culture with this invention for 5 days.

FIG. 2B is an SEM picture of osteoblastoma culture with this invention for 5 days.

FIG. 3A is a confocol picture of 3T3 (fibroblast cell) culture with this invention for 5 days.

FIG. 3B is an confocol picture of osteoblastoma culture with this invention for 5 days.

FIG. 4 is a H&E stain picture of osteoblastoma cell culture with this invention for 5 days.

DETAILED DESCRIPTION OF THE INVENTION

Reference will now be made in detail to the present embodiments of the invention, examples of which are illustrated in the accompanying drawings.

Figure 1:
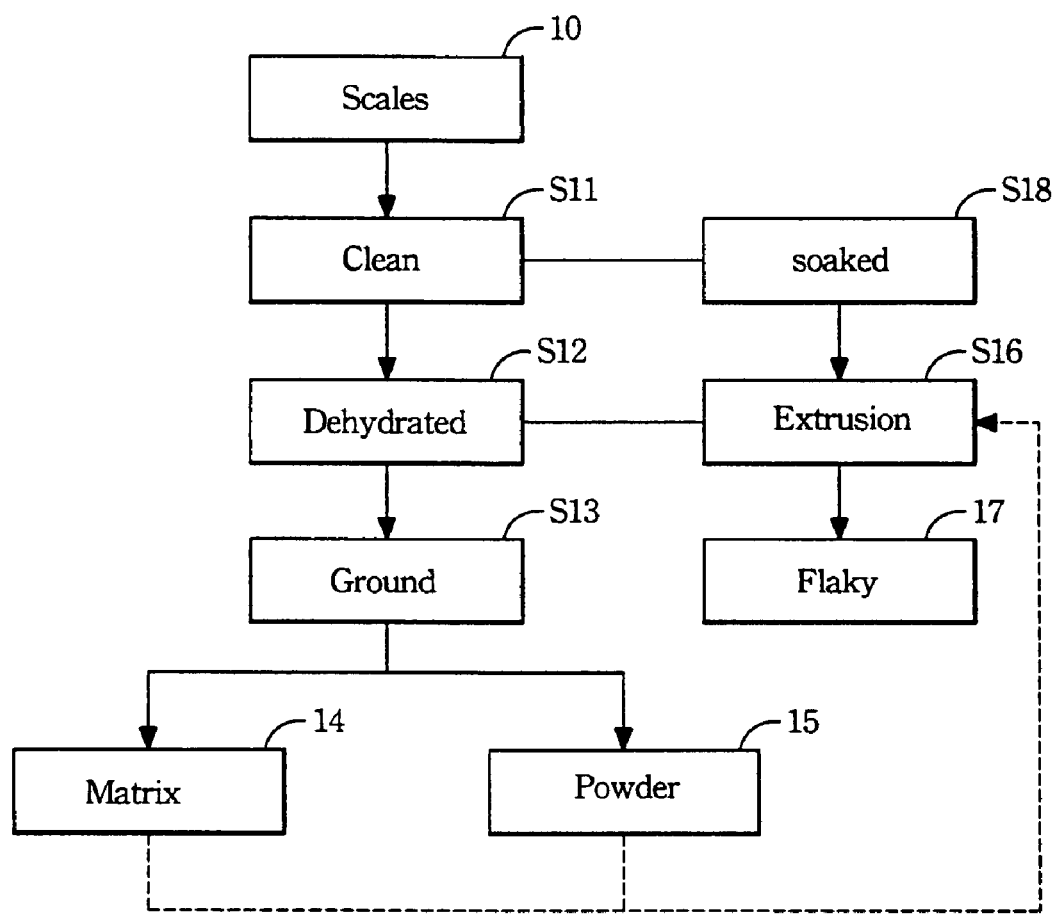

Referring to FIG. 1A, the present invention relates to a biomaterial prepared from fish scales 10. The biomaterial is prepared by a process which comprises dehydrating the fish scales 10 (S12) until the fish scales 10 contain less than about 50% of water. The dehydrated fish scales 10 are then ground (S13) into a ground product having a particle size of less than about 10,000 µm. In an embodiment of the invention, the fish scales 10 contain less than about 25% of water, and the ground particles have an average size of less than about 5,000 µm in diameter.

In accordance with some examples of the invention, the fish scales 10 may be freshly provided in a chilled or frozen manner. In a specific example of the invention, the fish scales 10 each having an average size less than about 20 cm in diameter may be selected for preparing the biomaterial. Prior to dehydration of the fish scales, the fish scales 10 may be cleaned by washing (S11) in a steam with other cleaning agents including but not limited to surfactant, detergent, warm water and polar solvent such as ethanol at about 60° C. However, the present invention is not limited to any particular cleaning step. For example, the fish scales are clean enough to pass Limulus Amebocyte Lysate (LAL) test which is an assay for detection and quantitation of bacterial endotoxin. Preferably, the cleaned fish scales would have a LAL test score less than about 100 Eu/ml.

According to one example of the invention, the fish scales 10 may be dehydrated (S12) (but not limited) after they are cleaned (S11) as described above. The fish scales may be dehydrated by air spraying, oven, freeze drying or any other conventional dehydration methods available so far. Also, the fish scale may be dehydrated by soaking the fish scales in the ethanol or other polar organic solvent. The fish scales are dehydrated until their water content is less than about 50%, preferably less than about 25%. According to another example of the invention, the dehydrated fish scales may be ground into particles each having an average size of less than about 10,000 μm, preferably about 5000 μm, in diameter. The ground particles may contain a mixture of sponge like matrix 14 and powder 15. For example, the ground particles may be further filtered using an optimal sieve to isolate the matrix and powder. The filtering step may be carried out with an aid of a vibrating means to enhance the sieving effect. As a result, the particles filtered out from the sieve provide the biomaterial in a powder form, whereas the filtrate that remains from the filtering step makes up the biomaterial in a matrix form. Also, the device adopted for grinding the fish scales are not limited to using any particular grinder, grinding machine or any equipment used to reduce the particle size of the fish scales, as long as each of the ground particles does not exceed an average size of less than about 10,000 μm, preferably less than about 5000 μm, in diameter.

These products may be further processed, for example, by extrusion (S16), filtering, fully or partially drying and sterilizing to yield sterilized biomaterials. In a preferred embodiment, these steps may be performed with or without heating. These products may be used in combination with a variety of connective tissue repair compositions, or in combination with other active or inactive ingredients.

In one other example, the dehydrated fish scales may be subjected to a heat treatment, such as a extrusion process performed at a temperature of less than about 200° C., preferably, about from 110° C. to 200° C., to produce the biomaterial in a flaky form. As one specific example, the dehydrated fish scales may be subjected to the extrusion with or without one or more cross linking ingredients. However, the present invention is not limited to the above method for producing the biomaterial in the flaky form. For example, the fish scales may also be subjected to a extrusion process performed at the temperature of less than about 200° C. after the cleaning step (S11) to produce the biomaterial in flaky form 17. An additional step (S18) of soaking the fish scales in water is selectively performed before the extrusion process (S16), but after the cleaning step (S11). Moreover, in yet another example of the invention, the biomaterials in the matrix 14 or powder form 15 may be further subjected to a extrusion process (S16) performed at a temperature of less than about 200° C. to convert into the biomaterial in the flaky form 17. However, the heat treatment in the present invention is not limited to the extrusion described above. One skilled in the art may also adopt other heat treatments such as thermal extrusion of any type, thermal pressing and molding steps to produce the flaky biomaterial.

The biomaterial of the invention contains tissue repair factors and may be manufactured into a tissue repair material for repairing a variety of tissue damages and tissue defect sites. For example, the biomaterial of the invention may be prepared for injection or insertion at, into, onto or near bone defect sites, cartilage repair sites, dental alveolar repair site or other soft tissue defect sites. In other examples, the biomaterial may be made as a coating material coated on surgical grafts or implants to be implanted at, into, onto or near bone defect sites, cartilage repair sites or other tissue defect sites. Accordingly, the invention is also applicable to connective tissue surgical implant with the tissue repair material derived from fish scales, whereby the surgical implant is implanted at a connective tissue defect site.

Summarizing from the above, the invention relates to a biomaterial in powder and/or matrix and/or flaky form prepared from the fish scales for use in a variety of tissue repairs and implantations. These fish scale derived products, also referred to herein as the biomaterial in a powder form, matrix form or flaky form may contain tissue repair factors and may be further processed to produce a variety of formulations and consistencies.

The invention will now be described in further detail with reference to the following specific, non-limiting examples.

Example 1

Matrix Form

Figure 1B:
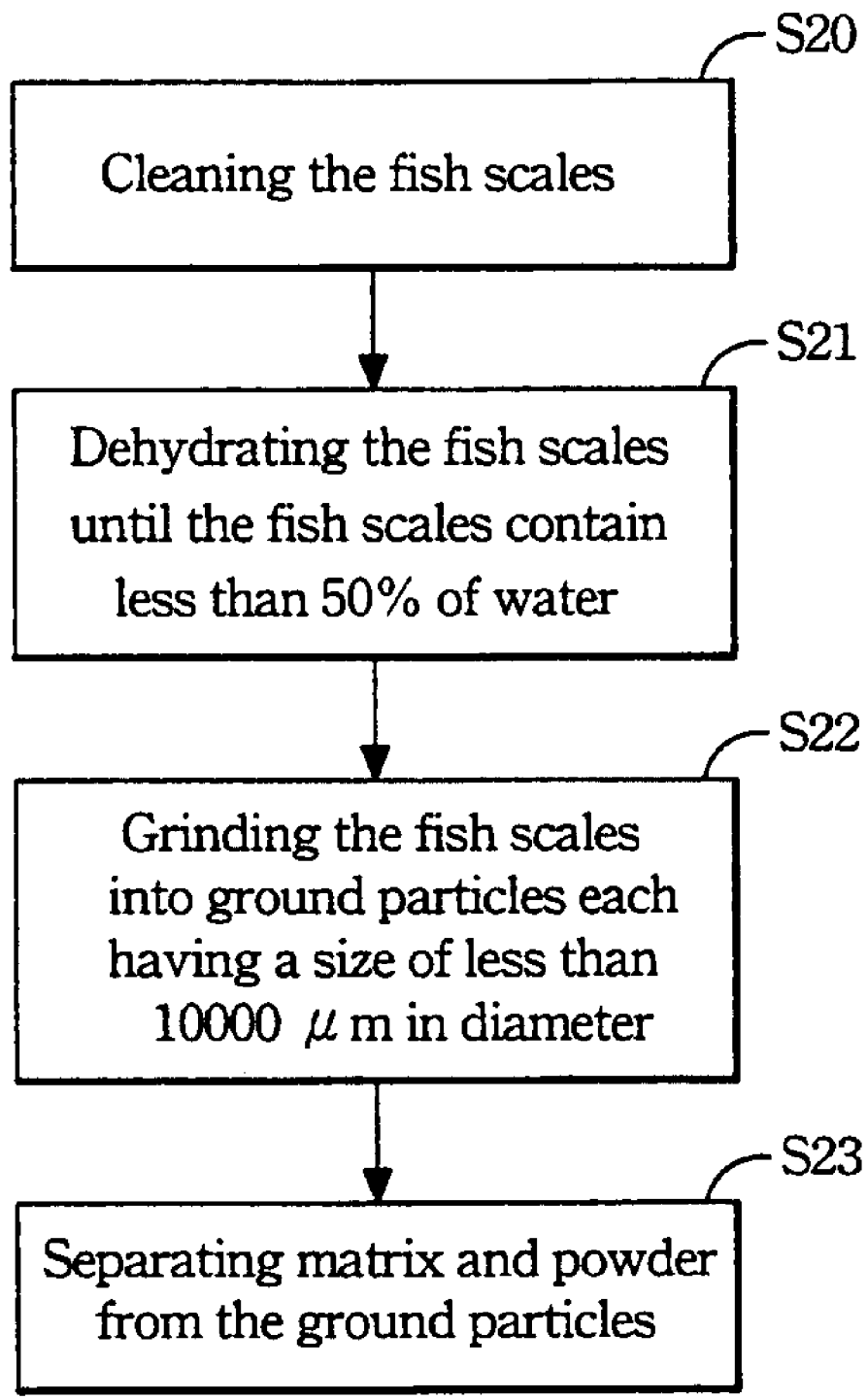

Referring to FIG. 1A and FIG. 1B, the process for preparing the biomaterial in a matrix form from fish scales begins with step (S20), where the fish scales are cleaned with a steam or vapor, for example, until the clean fish scales have a LAL test score of less than about 200 Eu/ml. The process then proceeds to step (S21). In step (S21), the fish scales are dehydrated until the fish scales contain less than 25% of water. Next, in step (S22), the dehydrated fish scales are ground into particles each having an average size of less than 5000 μm in diameter. The ground particles contain a mixture of sponge like matrix and powder. The process proceeds to step (S23). In step (S23), a filtering step is carried out using an optimal sieve for separating the matrix from the mixture. Accordingly, the filtrate from the filtering step makes up the matrix. The matrix contains fibrous tissue that is composed of HAP, TCP and collagen. The size of the fibrous is less than 2.5 mm in diameter.

Example 2

Powder Form

Referring to FIG. 1A and FIG. 1B again, the process for preparing the biomaterial in a powder form is similar to that for the biomaterial in matrix form except that the biomaterial in powder form include the particles filtered out and left on the sieve after the filtering step is carried out. Therefore, the powder form differs from the matrix form in that the powder form has a definite or mechanical structure. And the powder size is less than 5000 μm in diameter.

Example 3

Flaky Form

Figure 1C:
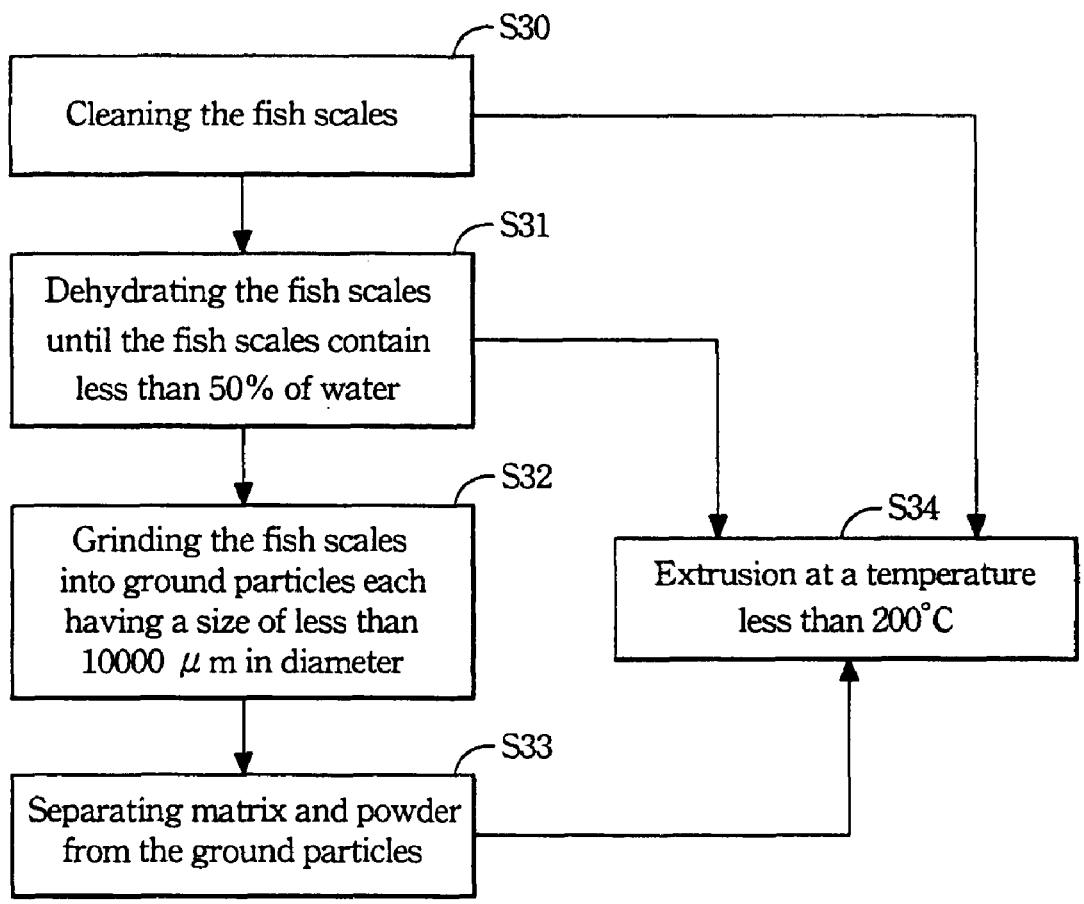

There are a number of ways for preparing the biomaterial in flaky form from the fish scales according to the process flow illustrated in FIG. 1A and FIG. 1C. Referring to FIG. 1A and FIG. 1C, a process for preparing the biomaterial in a flaky form from fish scales begins with step (S30), where the fish scales are cleaned with a steam or vapor, for example, until the clean fish scales have a LAL test score of less than about 200 Eu/ml. The process then proceeds to step (S31). In step (S31), the fish scales are dehydrated until the fish scales contain less than 25% of water. Next, in step (S32), the dehydrated fish scales are ground into particles each having an average size of less than 5000 μm in diameter. The ground particles contain a mixture of sponge like matrix and powder. The process proceeds to step (S33). In step (S33), a filtering step is carried out using an optimal sieve for separating the matrix and powder from the mixture. The process proceeds to step (S34) which includes subjecting the matrix and powder to extrusion.

Alternatively, the process for preparing the biomaterial in flaky form may proceed directly to step (S34) after the cleaning step to simplify the overall process. Also, the process may include the cleaning and dehydration steps before performing the extrusion step on the cleaned and dehydrated fish scales as shown in FIG. 1C.

Accordingly, the dehydrated fish scales, cleaned fish scales without dehydration, or the biomaterials derived from the fish scales in matrix or powder form are subjected to the extrusion step to produce the biomaterial in flaky form. The intact fish scales or different types of biomaterials derived from fish scales, previously cold pressed with a pressure of more than 100 g in 2.5 $cm^3$, preferably, more than 1 kg in 2.5 $cm^3$, are submitted to hot pressing performed at a temperature of less than about 200° C. in a desired mold. The cross linking of the biomaterials can be achieved physically by heating or chemically by adding with a cross linker at an optimal concentration before extrusion is performed. The cross linker is reactive with the amines group or other reactive group in the biomaterials.

Figure 2A:
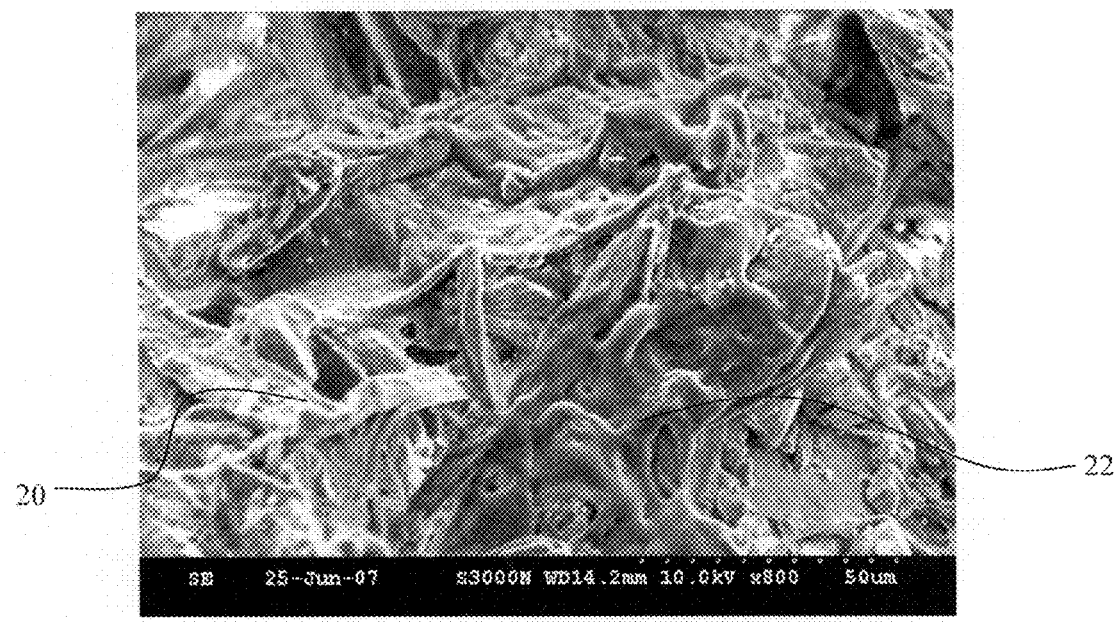
Figure 2B:
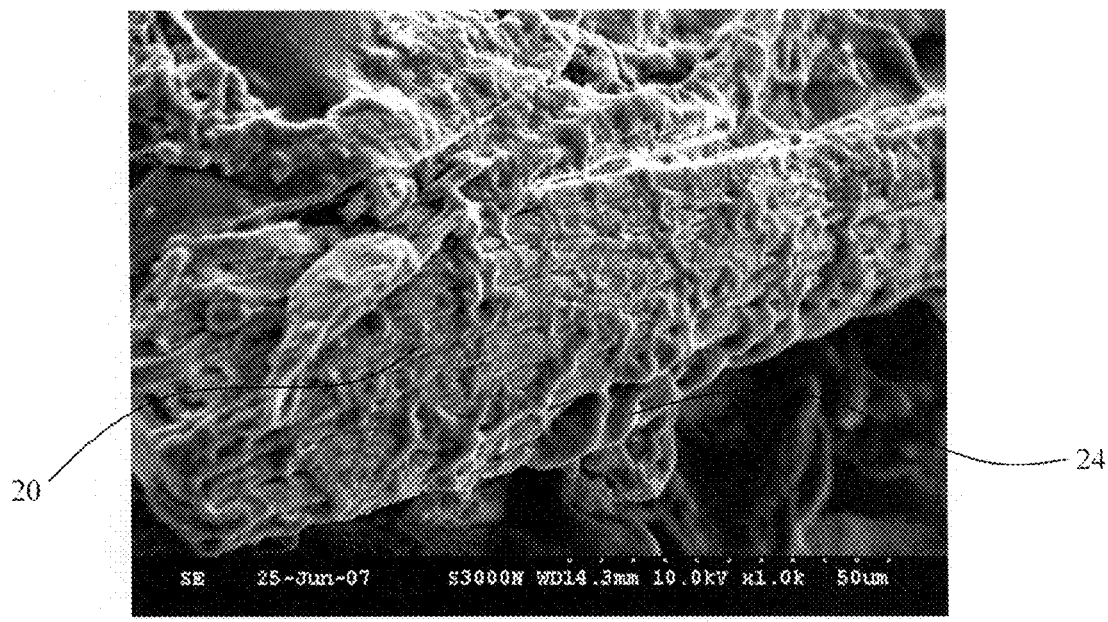

FIG. 2A is an SEM picture of 3T3 (fibroblast cell 22) culture with the biomaterial 20 described in present invention for 5 days. FIG. 2B is an SEM picture of osteoblastoma 24 culture with the biomaterial 20 described in the present invention for 5 days. These pictures show that cells (fibroblast 22 or osteoblastoma 24) can grow well on the biomaterial 20 described in the present invention.

FIG. 3A is a confocol picture of 3T3 (fibroblast cell) culture with this invention for 5 days. FIG. 3B is an confocol picture of osteoblastoma culture with this invention for 5 days. These pictures show that cells (fibroblast or osteoblastoma) can grow well on this invention.

Figure 4:
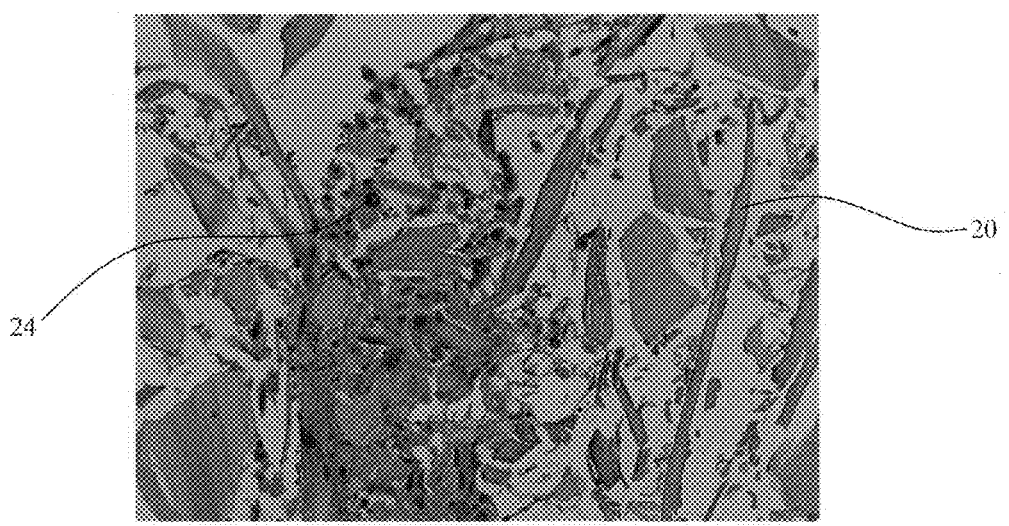

FIG. 4 is a H&E stain picture of osteoblastoma cell 24 culture with the biomaterial 20 described in the present invention for 5 days. These pictures show that osteoblastoma cell 24 can growth well on the biomaterial 20 described in the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A tissue repair biomaterial prepared from fish scales, comprising: a mixture of sponge made of fibrous tissue and powder-prepared by grinding a fish scale and the characteristic of said biomaterial is a LAL value below 200 Eu/mL.

2. The biomaterial according to claim 1, wherein the scale has an average diameter of less than 20 cm.

3. The biomaterial according to claim 1, wherein the mixture of fibrous tissue form and powder form have an average size of less than about 10,000 μm in diameter.

4. A biomaterial of tissue repair material prepared from fish scales, comprising: a flaky form prepared by subjecting at least one fish scale to an extrusion process, wherein said flaky form has a cross linking ingredient and the characteristic of said biomaterial is a LAL value below 200 Eu/mL.

* * * * *